United States Patent [19]

Nieves Elvira et al.

[11] Patent Number: 5,229,509
[45] Date of Patent: Jul. 20, 1993

[54] PROCESS FOR THE PREPARATION OF 3-CHLORO-CEFEM COMPOUNDS

[75] Inventors: Rosa M. Nieves Elvira; Santiago Conde Ruzafa; José R. Fernandez Lizarbe, all of Madrid, Spain

[73] Assignee: Antibioticos, S.A., Spain

[21] Appl. No.: 849,819

[22] Filed: Mar. 11, 1992

Related U.S. Application Data

[63] Continuation of Ser. No. 462,411, Jan. 9, 1990, abandoned.

[30] Foreign Application Priority Data

Jan. 10, 1989 [ES] Spain .................................. 8900071

[51] Int. Cl.$^5$ ............................................ C07D 501/04
[52] U.S. Cl. ...................................... 540/218; 540/215
[58] Field of Search ............................... 540/215, 218

[56] References Cited

U.S. PATENT DOCUMENTS

| | | | |
|---|---|---|---|
| 3,691,188 | 9/1972 | Spry | 540/218 |
| 3,714,146 | 1/1973 | Gottstein et al. | 540/218 |
| 3,925,372 | 12/1975 | Chauvette | 540/218 |
| 4,113,940 | 9/1978 | Kamiya et al. | 540/218 |
| 4,473,567 | 9/1984 | Ko'oka et al. | 540/218 |
| 4,513,134 | 4/1985 | Kim et al. | 540/218 |

OTHER PUBLICATIONS

Advanced Organic Chemistry by Jerry March pp. 382–384, 2nd edition McGraw Hill Book Company (1977).
Pharmazeutische Wirkstoffe, von A. Kleeman, Georg Thieme Verlag, Stuttgart and New York, 1982.
Biochemicals, Organic Compounds For Research and Diagnostic Reagents, Sigma Chemical Company, pp. 112 and 230 (1991).
S. Kukolja, J. Chem. Soc. 28: 181 (1977).

Primary Examiner—Thurman K. Page
Assistant Examiner—Jyothsna Venkat
Attorney, Agent, or Firm—Sterne, Kessler, Goldstein & Fox

[57] ABSTRACT

The process comprises a series of stages essentially comprising the protection of the functional groups of the side chain of Ampicillin, esterification of the acid group, oxidation to sulphoxide, expansion of the thiazole ring to a thiazine ring, ozonolysis of the exomethylene cefam derivative obtained, substitution of the hydroxyl group by chlorine and de-protection of the functional groups, in which the order of some stages can be varied without affecting the final result.

25 Claims, No Drawings

PROCESS FOR THE PREPARATION OF 3-CHLORO-CEFEM COMPOUNDS

This application is a continuation of application Ser. No. 07/462,411, filed Jan. 9, 1990, now abandoned.

TECHNICAL FIELD OF THE INVENTION

The present invention relates to a process for preparing a 3-chloro-cefem compound, its esters and pharmaceutically acceptable salts, starting from a compound which can be easily dried as it is 6-(α-aminophenylacetamide)-penicillanic acid, by means of a sequence of reactions on the amino-phenylacetamide group, which leads to a 3-chloro-cefem with the amino-phenylacetamide grouping in position 7, thereby producing compounds of importance in human and veterinary medicine.

STATE OF THE ART

The procedures hitherto described for the preparation of 3-chloro-cefem compounds, to which the present invention relates, start from penam or cefem compounds, in which the side chain is inter alia phenoxyacetyl or thienylacetyl, which has to be removed in order to be substituted by α-aminophenylacetyl, by means of hydrolysis and subsequent acylation.

The present invention introduces the novelty that the entire sequence of reactions which leads to the aforesaid 3-chloro-cefem compounds is performed with the radical α-amino-phenylacetyl duly protected, which appreciably reduces the number of stages required for its preparation, simplifying its industrial application.

DETAILED DESCRIPTION OF THE INVENTION

The present invention relates to a process for the preparation of 3-chloro-cefem compounds and, more particularly, (6R, 7R)-7-[(R)-2-amino-2-phenylacetamido]-3-chloro-8-oxo-5-thia-1-azabicyclo[4,2,0]-oct-2-ene-2-carboxylic acid, as well as its salts or derivatives of therapeutic or industrial application, characterized by the general formula

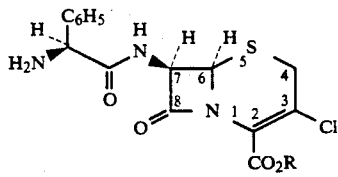

(I)

in which R represents a hydrogen atom or a therapeutically acceptable organic or metallic cation.

The compound of the general formula I has been named in the first paragraph in accordance with the official rules of nomenclature of IUPAC (International Union of Pure and Applied Chemistry) based on the number system:

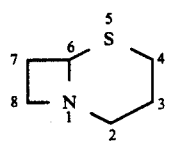

of the heterocyclic system 5-thia-1-azabicyclo[4,2,0]octane, corresponding to derivatives of cephalosporin, in the same way that the system 4-thia-1-azabicyclo[3,2,0]heptane and the number system:

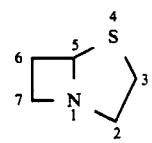

corresponds to derivatives of penicillin. From here onwards the following number systems will be used:

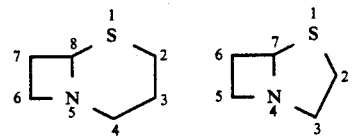

derived from the cefam and penam systems, much more common in the field of antibiotics, and the official nomenclature of IUPAC is only used in the titles of the compounds in the experimental part.

The compounds of formula I, of which a preparation process is claimed, include the known antibiotic Cefaclor in which R=H, described in U.S. Pat. No. 3,925,372. It is a cephalosporin of wide antibacterial range as described in Antimicrob. Agents Chemother. 12 591 (1977) and 14 614 (1978). This antibiotic has the important characteristic that, in addition to being active in parenteral administration, for example subcutaneous or intramuscular, it is also effective when administered orally. This property makes it particularly useful in the treatment of bacterial infections, both in human and equally in veterinary medicine.

The procedures described up till now are based on obtaining compounds of the general formula II

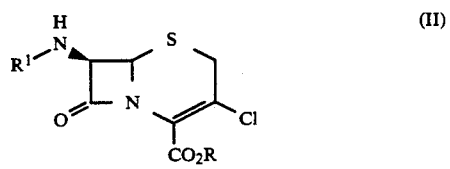

(II)

in which R has the value indicated above and $R^1$ represents an acylating group, in general one of those generally used in the field of penicillins and cephalosporins, for example phenoxyacetyl or thienylacetyl, of formulae III and IV respectively.

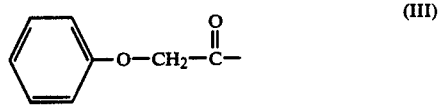

(III)

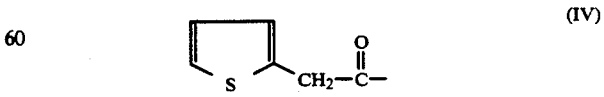

(IV)

These compounds of general formula II must undergo a process of hydrolysis to eliminate the acylating chain of the amine group in position 7, normally the radicals III or IV, to produce the basic compounds of general formula V:

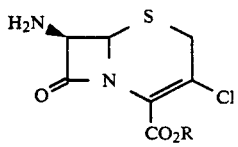
(V)

These compounds V must be subjected to a new acylation to introduce the radical D-2-amino-2-phenyl-acetyl VI:

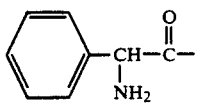
(VI)

and finally yield the already mentioned compounds of the general formula I.

The procedure described in the present invention provides the interesting novelty that the entire sequence of reactions which leads to the compounds of the general formula I is carried out with the radical D-2-amino-2-phenylacetyl (VI), duly protected, as an acylating chain of the amine group at 7 ($R^1$ in II). In this way, the long sequence of reactions is substantially shortened, by avoiding the hydrolysis of the side chain of II and the subsequent acylation of V.

The chemical name of the starting product for this synthesis according to the systematic nomenclature of IUPAC is 6-[(R)-2-amino-2-phenylacetamido]-3,3-dimethyl-7-oxo-4-thia-1-azabicyclo[3,2,0]heptane-2-carboxylic acid (VII) or 6-(α-aminophenyl-acetamido)-penicillanic acid, a very well-known and easily available semi-synthetic penicillin.

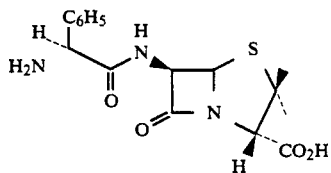
(VII)

The procedure which forms the subject of this patent is characterized by the following stages:

STAGE 1

Ampicillin acid is dissolved in acetone with a basic compound, preferably a tertiary amine, to produce an imidazole derivative of formula VIII:

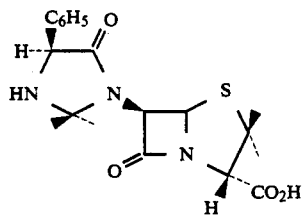
(VIII)

This compound VIII is treated, without previous purification with sodium nitrite, in a two-phase system, at a moderately acid pH, to provide high yields of a crystalline product, the formula of which is represented as IX:

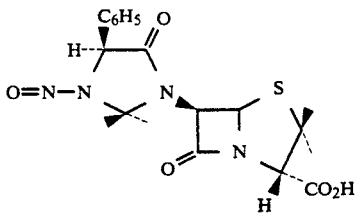
(IX)

STAGE 2

The compound IX is esterified by reaction with a halogen derivative, such as an alkyl or benzyl halide, in an aprotic polar medium, such as that provided by the solvents dioxan, tetrahydrofuran, acetone, N,N-dimethylformamide or mixtures thereof. This solution is treated with a weak alkaline agent, such as sodium bicarbonate or potassium bicarbonate, compounds of general formula X being obtained:

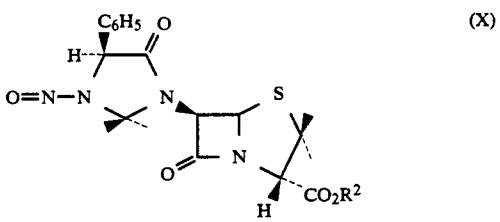
(X)

The radical represented by $R^2$ forms an ester group with the carboxylic acid in position 3 of the penam bicyclic system and should have the characteristics of giving greater stability to the molecule, blocking or protecting the carboxyl group and enhancing the solubility of the various compounds which are formed in the sequence of reactions constituting the subject of the present invention. In addition, it should be easy to eliminate by a simple chemical reaction such as reduction, or chemical or enzyme hydrolysis. By way of example, the chemical groups methyl, benzyl or para-nitrobenzyl can be named. These examples should not be taken as a limitation of the patent, since any other group which meets the requirements set out above is also included in the patented procedure.

This radical $R^2$ retains the value indicated in the preceding paragraph in the description of the following stages of the procedure forming the subject of the patent.

These compounds need not be separated and purified, but are directly subjected to oxidation by treatment of the solution of the said esters X with a per-acid or peroxide, in any of the solvents normally used in these reactions, such as methylene chloride, methanol, acetone, or mixtures thereof, cooled to low temperature. High yields of the (R) sulphoxides of the general formula XI are obtained:

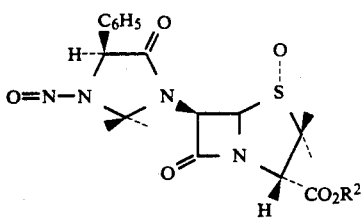

(XI)

These sulphoxides are separated as crystalline solids having precise melting points.

STAGE 3

This is characterized by the expansion of the 5-membered penam ring to the six membered cefem, by way of a monocylic intermediary which it is not necessary to separate.

The sulphoxides of general formula XI, obtained in the previous stage, are dissolved in a hydrocarbon solvent such as benzene or toluene, or a chlorinated solvent such as chloroform or 1,2-dichloroethane, and are made to react by heating with an N-haloamide or N-haloimide, such as N-chloroacetamide, N-chlorosuccimide or N-chlorophthalimide. This treatment opens the thiazolidine ring, producing a monocyclic sulphinyl chloride of the general formula XII which is not separated:

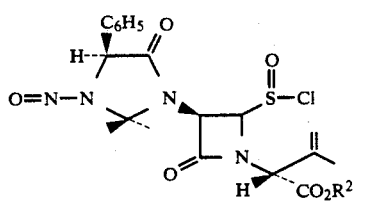

(XII)

and which is immediately treated with a compound of the group known in chemistry as Lewis acids, such as aluminium chloride, zinc bromide or tin (IV) chloride. The reaction product is precipitated as an aggregation complex with a metallic salt. Starting from this complex, of unknown formula, the 3-exomethylene cefam-S-oxide of the general formula XIII is obtained,

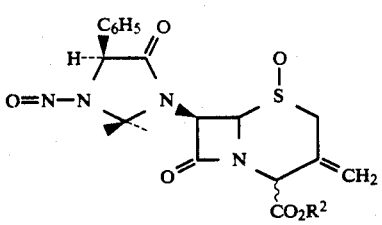

(XIII)

in which $R^2$ has the same value as a mixture of both isomeric sulphoxides R— and S—. The separation of the sulphoxides, starting from the metallic complex, is carried out by treatment of the latter with any molecule with free electron pairs, such as alcohols (methanol, ethanol, isopropanol) or ethers (diethyl ether, tetrahydrofuran).

STAGE 4

The mixture of the two S-oxides or isomeric sulphoxides of the 3-exomethylene cefam XIII is subjected to ozonolysis, in solution in any solvent customary for these reactions, such as methanol, acetone, methylene chloride or mixtures thereof. This reaction is carried out at low temperature, in a bath of acetone/dry ice. The ozonide formed is destroyed by any of the usual chemical procedures, such as for example treatment with sulphur dioxide, sodium bisulphite, dimethyl sulphide, possibly including simple heating. High yields of the mixture of isomeric S-oxides of the 3-hydroxycefem compound of formula XIV are obtained:

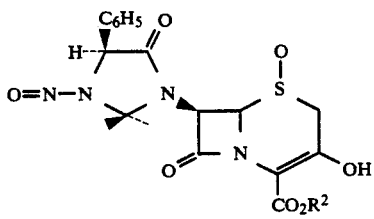

(XIV)

STAGE 5

This stage is characterized by the fact that three reactions take place which are effected by the use of the Vilsmeier reagent, which acts simultaneously as a halogenating agent and as a reducing agent. By treating the 3-hydroxy cefem-S-oxide XIV with the aforesaid reagent, the hydroxyl group in position 3 of the cefem ring undergoes a 3-chloro substitution reaction, resulting in the product of the general formula XV

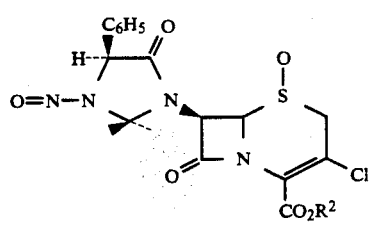

(XV)

which can be separated when work is performed at low temperatures. Under normal working conditions two other reactions take place simultaneously: the reduction of the S-oxide group to sulphide and the reductive denitrosation of the nitroso group which protects the secondary amine which constitutes position 3 of the imidazolidine ring in the side chain, a compound of formula XVI being produced in a single stage:

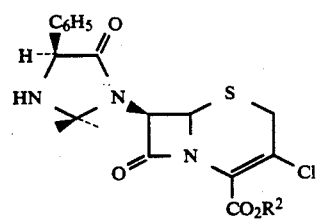

(XVI)

This product is in fact the molecule of the required antibiotic with protective or blocking groups on the carboxyl and on the side chain.

STAGE 6

In this final stage the compound XVI is subjected to deblocking of the carboxyl group, by any type of reduction or hydrolysis, according to the nature of the esterifying radical $R^2$. In the case of hydrolysis, deprotection of the side chain also takes place simultaneously to produce the required antibiotic in the form of a monohydrate, by precipitation at its iso-electric point. In the case where deblocking of the carboxyl group is carried out by hydrogenolysis, the subsequent hydrolysis is performed in a single step, without separating or purifying any intermediate product. In this final stage the compound I is obtained in which R represents hydrogen which can subsequently be substituted by an alkali metal or any other salt, inorganic or organic.

The overall chemical reaction scheme which constitutes the process forming the subject of the present invention, separated into its various stages, is as follows:

Stage 1

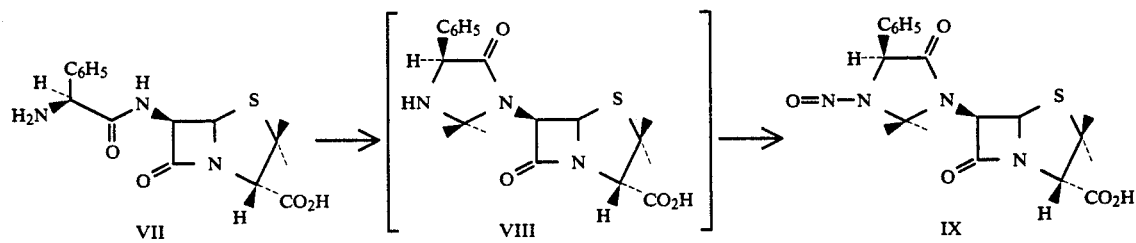

Stage 2

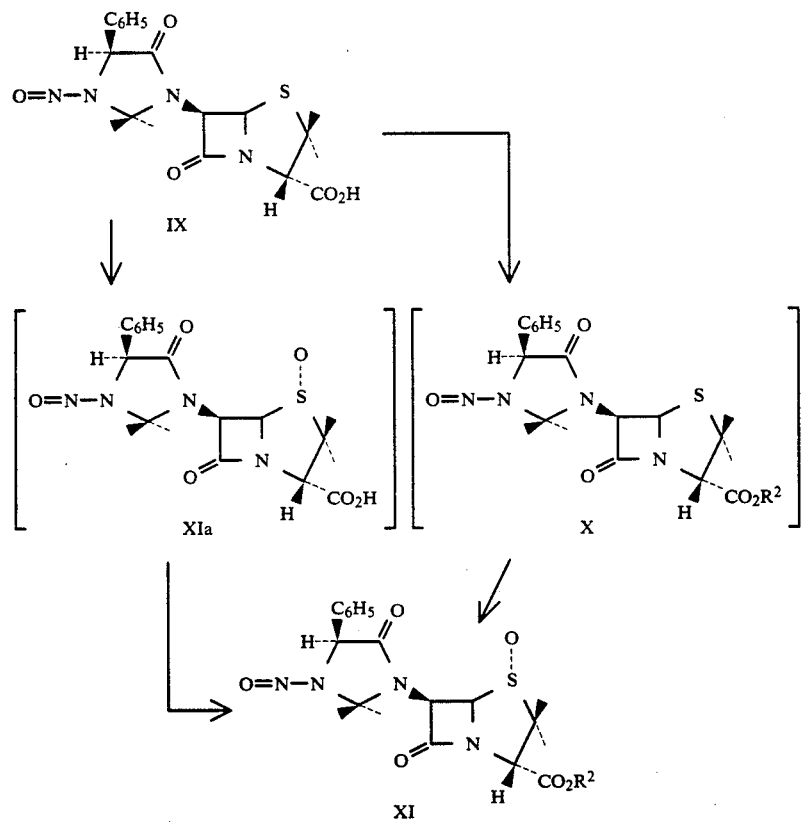

Stage 3

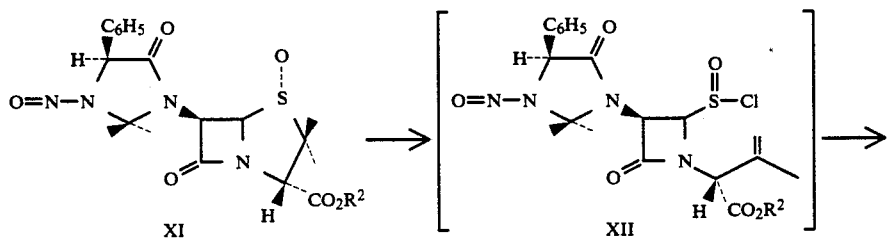

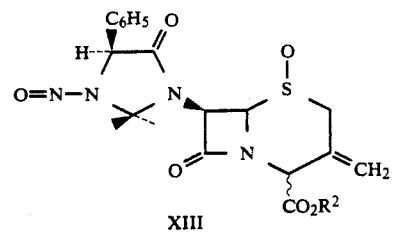

Stage 4

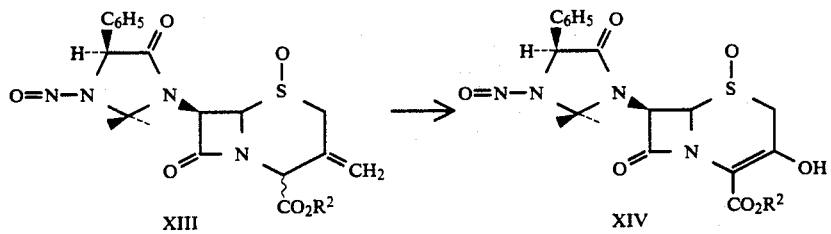

Stage 5

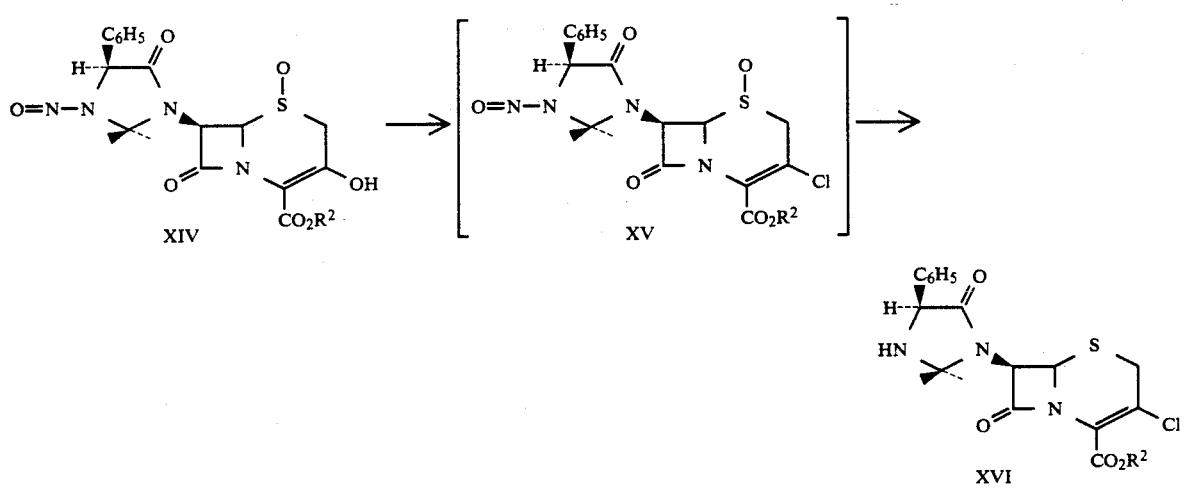

Stage 6

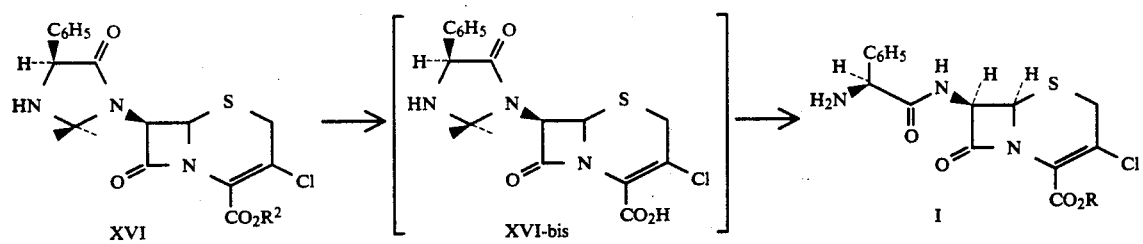

This scheme should not be taken as being exclusive, but rather explanatory, since the order of any chemical stages can be varied without affecting the general process, for example in Stage 2, the order in which the reactions of esterification and oxidation are performed is immaterial to the end result.

The intermediate products in question are indicated in square brackets in accordance with the general notation of organic chemistry. The fact that they are not separated should not be interpreted as meaning that they cannot be separated, but that it is not necessary to do it and so the process becomes simpler by including various steps in a single stage.

Examples to illustrate in detail the procedure which forms the subject of this invention are given below. These examples should not be taken as being a limitation of the scope of the patent, but as typical experimental cases of the general procedure.

EXAMPLE 1

(6R,7R)-7-[(R)-2-AMINO-2-PHENYLACETAMIDO]-3-CHLORO-8-OXO-5-THIA-1-AZABICYCLO[4,2,0]OCT-2-ENE-2-CARBOXYLIC ACID 1. (5R, 6R, 4'R)-6-(2',2'-Dimethyl-3-nitroso-5'-oxo-4'-phenyl-imidazolidin-1'-yl)-3,3-dimethyl-7-oxo-4-thia-1-azabicyclo[3,2,0]heptane-2-carboxylic acid.

2.6 ml (18.6 mmol) of triethylamine are added to a suspension of 3.5 g (10 mmol) of ampicillin in 15 ml of acetone and stirring takes place for 20 hours, at room temperature. After evaporating the solvent, 30 ml of water, 0.83 g (12 mmol) of sodium nitrite and 20 ml of ethyl acetate are added. The mixture is cooled in an ice bath and is acidified with hydrochloric acid to a pH of 2. The aqueous phase is decanted and the organic phase is washed successively with water and saturated sodium chloride solution, dried over anhydrous magnesium sulphate and evaporated to dryness. A white solid is obtained which corresponds to the title compound. It crystallizes from methanol/water. M.p. 167°-169° C.

IR (Nujol) $\nu = 1800$ (C=O $\beta$-lactam), 1740 (CO$_2$H), 1720 (C=O imidazolidine) 1440 (N—N=O) and 1090 cm$^{-1}$ (N—N=O) $^1$H-NMR (DMSO-d$_6$) $\delta = 13.3$ (br.s., 1H, —CO$_2$H, interchanges D$_2$O), 7.3 (m, 5H, C$_6$H$_5$), 5.65 (S, 1H, CH—C$_6$H$_5$), 5.6 (d, J=4.5 Hz, 1H, H-6), 5.4 (d, J=4.5 Hz, 1H, H-5), 4.35 (s, 1H, H-2), 2.05 (s, 3H, CH$_3$ imidazoline), 2.0 (s, 3H, CH$_3$ imidazoline), 1.5 (s, 3H, CH$_3$ $\beta$) and 1.4 ppm (s, 3H, CH$_3$ $\alpha$) UV (MeOH) $\lambda$ max.=205 and 218 nm.

2. p-Nitrobenzyl (5R, 6R, 4'R)-6-(2',2'-dimethyl-3'-nitroso-5'-oxo-4'-phenyl-imidazolidin-1'-yl)-3,3-dimethyl-7-oxo-4-thia-1-azabicyclo[3,2,0]heptane-2-carboxylate.

A suspension of 4.2 g (10 mmol) of (5R,6R,4'-R)-6-(2',2'-Dimethyl-3'-nitroso-5'-oxo-4'-phenyl-imidazolidin-1'-yl)-3,3-dimethyl-7-oxo-4-thia-1-azabicyclo[3,2,0]heptane-2-carboxylic acid in a mixture of 50 ml of N,N-dimethylformamide and 40 ml of dioxan is treated with 0.9 g (10.7 mmol) of sodium bicarbonate and 2.4 g (11 mmol) of p-nitrobenzyl bromide for 24 hours, at room temperature. Next, 50 ml of water and 100 ml of ethyl acetate are added. The organic phase is decanted, and is washed with water and is dried over anhydrous magnesium sulphate. A solid is obtained by evaporation to dryness, which is crystallized from isopropanol and the analytic data of which correspond to the title product. M.p. 97°-99° C.

IR (Nujol) $\nu = 1800$ (C=O $\beta$-lactam), 1740 (C=O imidazolidinyl), 1700 (CO$_2$R), 1510, 1320 (NO$_2$), 1460 (N—N=O) and 1080 cm$^{-1}$ (N—N=O). $^1$H-NMR (CDCl$_3$) $\delta = 7.9$ (q, 4H, C$_6$H$_4$), 7.25 (m, 5H, C$_6$H$_5$), 5.65 (d, J=4 Hz, 1H, H-6), 5.45 (s, 1H, —CH—C$_6$H$_5$), 5.25 (s, 2H, CH$_2$), 4.95 (d, J=4 Hz, 1H, H-5), 4.6 (s, 1H, H-2), 2.1 (s, 6H, 2CH$_3$ imidazoline), 1.6 (s, 3H, CH$_3$ $\beta$) and 1.4 ppm (s, 3H, CH$_3$ $\alpha$). UV (CHCl$_3$) $\lambda$ max.=235 and 260 nm.

3. p-Nitrobenzyl (4R,5R,6R,4'R)-6-(2',2'-dimethyl-3'-nitroso-5'-oxo-4'-phenyl-imidazolidin-1'-yl)-3,3-dimethyl-7-oxo-4-thia-1-azabicyclo[3,2,0]heptane-2-carboxylate 4-oxide.

An ozone current is passed through a solution of 5 g of p-nitrobenzyl (5R,6R,4'R)-6-(2',2'-dimethyl-3'-nitroso-5'-oxo-4'-phenyl-imidazolidin-1'-yl)-3,3-dimethyl-7-oxo-4-thia-1-azabicyclo[3,2,0]heptane-2-carboxylate in 100 ml of acetone for 45 minutes, while it is cooled in a bath of solid carbon dioxide. The title product is obtained in the form of a white solid by evaporation to dryness. M.p. 119°-121° C.

IR (Nujol) $\nu = 1800$ (C=O $\beta$-lactam), 1750 (C=O imidazolidinyl), 1710 (CO$_2$R), 1520, 1340 (NO$_2$), 1470 (N—N=O) and 1050 cm$^{-1}$ (SO). $^1$H-NMR (CDCl$_3$) $\delta = 7.9$ (q, 4H, C$_6$H$_4$), 7.35 (m, 5H, C$_6$H$_5$), 5.5 (s, 1H, CH—C$_6$H$_5$), 5.3 (s, 2H, CH$_2$) 5.1 (d, J=4 Hz, 1H, H-6), 4.8 (d, J=4 Hz, 1H, H-5), 4.55 (s, 1H, H-2), 2.2 (s, 3H, CH$_3$ imidazoline), 2.1 (s, 3H, CH$_3$ imidazoline), 1.6 (s, 3H, CH$_3$ $\beta$) and 1.2 ppm (s, 3H, CH$_3$ $\alpha$) UV (CHCl$_3$) $\lambda$max.=258 nm.

4. p-Nitrobenzyl (6R,7R,4'R)-7-(2',2'-dimethyl-3'-nitroso-5'-oxo-4'-phenyl-imidazolidin-1'-yl)-3-exomethylen-8-oxo-5-thia-1-azabicyclo[4,2,0]octane-2-carboxylate 5-oxide.

A mixture of 5.7 g (10 mmol) of p-nitrobenzyl (4R,5R,6R,4'R)-6-(2',2'-dimethyl-3'-nitroso-5'-oxo-4'phenyl-imidazolidin-1'-yl)-3,3-dimethyl-7-oxo-4-thia-1-azabicyclo[3,2,0]heptane-2-carboxylate 4-oxide, 200 ml of dry chloroform, 3.5 ml (50 mmol) of propylene oxide and 3 g (22 mmol) of N-chlorosuccinimide is stirred under reflux for 6 hours under dry nitrogen. Half the solvent is removed, and the mixture is cooled to precipitate the succinimide which is filtered off. The filtrate is evaporated to dryness and the residue obtained is dissolved in 40 ml of dry toluene. Next, a solution of 2.35 ml (20 mmol) of tin tetrachloride in 5 ml of dry toluene is slowly added and the mixture is stirred for 14 hours, at room temperature. The precipitate formed is filtered and washed successively with toluene and pentane. The solid obtained is suspended in 180 ml of cold ether and is stirred for 30 minutes. The suspension is filtered and precipitated from ethanol as a mixture of diastereoisomers of the title compound, which are separated by high-pressure liquid chromatography, using a mixture of ethyl acetate-hexane in a 2:1 proportion as an eluent.

The 5R sulphoxide is separated as a colourless foam.
IR (Nujol) $\nu = 1780$ (C=O $\beta$-lactam), 1720 (C=O imidazolidinyl), 1700 (CO$_2$R), 1520 and 1350 cm$^{-1}$ (NO$_2$).

$^1$H-NMR (CDCl$_3$) $\delta = 7.9$ (q, 4H, C$_6$H$_4$), 7.3 (m, 5H, C$_6$H$_5$), 5.7 (s, 1H, CH-C$_6$H$_5$), 5.6 (d, 1H, J=4.5 Hz, H-7), 5.35 (s, 2H, CH$_2$), 5.3 (s, 2H, =CH$_2$), 5.1 (d, 1H, J=4.5 Hz, H-6), 3.5 (q, 1H, H-2) and 2.3 ppm (s, 6H, 2CH$_3$ imidazoline) UV (CHCl$_3$) $\lambda$ max.=235 and 260 nm.

The 5S sulphoxide is separated in the form of a foam.
IR (Nujol) $\nu = 1780$ (C=O $\beta$-lactam), 1720 (C=O imidazolidinyl), 1700 (CO$_2$R), 1520 and 1350 cm$^{-1}$ (NO$_2$).

$^1$H-NMR (CDCl$_3$) $\delta = 7.9$ (q, 4H, C$_6$H$_4$), 7.3 (m, 5H, C$_6$H$_5$), 5.5 (s, 1H, CH—C$_6$H$_5$), 5.45 (s, 1H, =CH$_2$), 5.35 (s, 2H, CH$_2$), 5.25 (s, 1H, =CH$_2$), 5.2 (d, J=4.5 Hz, 1H, H-7), 4.8 (d, J=4.5 Hz, 1H, H-6), 3.5 (q, 1H, H-2), 2.15 (s, 3H, CH$_3$ imidazoline) and 2.05 ppm (s, 3H, CH$_3$ imidazoline) UV (CHCl$_3$) $\lambda$ max.=235 and 260 nm.

5. p-Nitrobenzyl (6R,7R,4'R)-7-(2',2'-dimethyl-3'-nitroso-5'-oxo-4'-phenyl-imidazolidin-1'-yl)-3-hydroxy-8-oxo-5-thia-1-azabicyclo[4,2,0]oct-2-ene-2-carboxylate 5-oxide.

A solution of 1 g (1.7 mmol) of p-nitrobenzyl (6R,7R,4'R)-7-(2',2'-dimethyl-3'-nitroso-5'-oxo-4'-phenyl-imidazolidin-1'-yl)-3-exomethylen-8-oxo-5-thia-1-azabicyclo [4,2,0]octane-2-carboxylate 5-oxide in 180 ml of methylene chloride is cooled in a bath of solid carbon dioxide and an ozone current is passed until blue coloration occurs. An oxygen current is then passed through for some minutes in order to remove the excess ozone and evaporation then takes place, so as to produce the product of the heading in the form of a white foam as a mixture of diastereoisomers in the form of a white foam.

IR (Nujol) $\nu=1780$ (C=O $\beta$-lactam), 1720 (C=O imidazolidinyl), 1700 (CO$_2$R) and 1200 cm$^{-1}$ (a, OH). $^1$H-NMR (CDCl$_3$) $\delta=7.9$ (q, 4H, C$_6$H$_4$), 7.3 (m, 5H, C$_6$H$_5$), 5.6 and 5.5 (s, 1H, CH-C$_6$H$_5$), 5.4 (s, 2H, CH$_2$), 5.1 and 5.05 (d, J=4.5 Hz, 1H, H-7), 4.8 and 4.6 (d, J=4.5 Hz, 1H, H-6), 4.0 and 3.6 (q, 2H, H-2), 2.2 (a, OH, interchanges D$_2$O), 2.3, 2.25, 2.2 and 2.15 ppm (s, 6H, 2CH$_3$ imidazoline).

6. p-Nitrobenzyl (6R,7R,4'R)-7-(2',2'-dimethyl-5'-oxo-4'-phenyl-imidazolidin-1'-yl)-3-chloro-8-oxo-1-aza-5-thiabicyclo[4,2,0]oct-2-ene-2-carboxylate.

A solution of 1.2 g (2 mmol) of p-nitrobenzyl (6R,7R,4'R)-7-(2',2'-dimethyl-3'-nitroso-5'-oxo-4'-phenyl-imidazolidin-1'-yl)-3-hydroxy-8-oxo-1-aza-5-thiabicyclo [4,2,0]oct-2-ene-2-carboxylate 5-oxide in 10 ml of dry N,N-dimethylformamide is cooled in a bath of solid carbon dioxide and is treated with a solution of 0.32 ml (4 mmol) of phosphorus trichloride in 4 ml of dry N,N-dimethylformamide. It is stirred for 1 hour below 0° C. and for 1 hour at room temperature. The reaction mixture is poured over ice water and the precipitate formed is filtered, washed with water several times and dried in a vacuum, yielding the product of the heading in the form of a foam.

IR (Nujol) $\nu=1800$ (C=O $\beta$-lactam), 1740 (C=O imidazolidinyl), 1720 cm$^{-1}$ (CO$_2$R). $^1$H-NMR (CD$_3$OD) $\delta=7.9$ (q, 4H, C$_6$H$_4$), 7.4 (m, 5H, C$_6$H$_5$), 5.4 (d, J=4.5 Hz, 1H, H-7), 5.2 (s, 1H, CH-C$_6$H$_5$), 5.35 (s, 2H, CH$_2$), 5 (d, J=4.5 Hz, 1H, H-6), 3.75 (q, 2H, H-2), 1.55 (s, 3H, CH$_3$ imidazoline) and 1.45 ppm (s, 3H, CH$_3$ imidazoline).

7. (6R, 7R)-7-[(R)-2-Amino-2-phenylacetamido]-3-chloro-8-oxo-5-thia-1-azabicyclo[4,2,0]oct-2-ene-2-carboxylic acid.

1.5 ml of trifluoroacetic acid is added to a solution of 0.54 g (1 mmol) of p-nitrobenzyl (6R,7R,4'R)-7-(2',2'-dimethyl-5-oxo-4'-phenyl-imidazolidin-1'-yl)-3-chloro-8-oxo-5-thia-1-azabicyclo[4,2,0]oct-2-ene-2-carboxylate in 1 ml of anisole cooled to 0° C., and stirring takes place for 30 minutes between 5° and 10° C. 50 ml of ether is added and the precipitate obtained is filtered, washed with ether and dried in a vacuum. This solid is treated in an aqueous medium. which is acidified at a pH of 4.5 with dilute hydrochloric acid, thereby precipitating the title product.

IR (Nujol) $\nu=1780$ (C=O $\beta$-lactam), 1690 (C=O amide), 1600 (CO$_2$H) and 697 cm$^{-1}$ (C—Cl). $^1$H-NMR (D$_2$O+Cl) $\delta=7.6$ (s, 5H, C$_6$H$_5$), 5.8 (d, J=5 Hz, 1H, H-7), 5.3 (s, 1H, CH-C$_6$H$_5$), 5.2 (d, J=5 Hz, 1H, H-6) and 3.7 ppm (q, 2H, H-2). UV (HCl 0.1M) $\lambda$ max.=230 and 265 nm.

EXAMPLE 2

P-NITROBENZYL (5R,6R,4'R)-6-(2',2'-DIMETHYL-3'-NITROSO-5'-OXO-4'-PHENYL-IMIDAZOLIDIN-1'-YL)-3,3-DIMETHYL-7-OXO-4-THIA-1-AZABICYCLO[3,2,0]HEPTANE-2-CARBOXYLATE 4-OXIDE (XI)

0.86 g (5 mmol) of m-chloroperbenzoic acid is added to a solution of 1.1 g (2 mmol) of p-nitrobenzyl (5R,6R,4'R)-6-(2',2'-dimethyl-3'-nitroso-5'-oxo-4'-phenyl-imidazolidin-1'-yl)-3,3-dimethyl-7-oxo-1-aza-4-thiabicyclo [3,2,0]heptane-2-carboxylate in 20 ml of methylene chloride, while cooling takes place in an ice bath. Stirring takes place for 3 more hours between 5 and 10° C., at the end of which the precipitate formed is filtered off and the filtrate is washed successively with water, a saturated sodium bicarbonate solution and a saturated sodium chloride solution. The organic phase is dried over anhydrous magnesium sulphate and by subsequent evaporation a white solid is obtained which corresponds to the compound in the heading.

EXAMPLE 3

METHYL (5R,6R,4'R)-6-(2',2'-DIMETHYL-3'-NITROSO-5'-OXO-4'-PHENYL-IMIDAZOLIDIN-1'-YL)-3,3-DIMETHYL-7-OXO-4-THIA-1-AZABICYCLO[3,2,0]HEPTANE-2-CARBOXYLATE (X)

A suspension of 4.2 g (10 mmol) of (5R,6R,4'R)-6-(2',2'-dimethyl-3'-nitroso-5'-oxo-4'-phenyl-imidazolidin-1'-yl)-3,3-dimethyl-7-oxo-4-thia-1-azabicyclo[3,2,0]heptane-2-carboxylic acid, 0.9 g (10.7 mmol) of sodium bicarbonate and 1.3 ml (21 mmol) of methyl iodide in 50 ml of N,N-dimethylformamide is stirred at room temperature for 24 hours, at the end of which it is poured over crushed ice. The white precipiate formed is washed with water and is dried in a vacuum. The said solid which corresponds to the title product is crystallized from methanol. M.p. 179°–181° C.

IR (Nujol) $\nu=1790$ (C=O $\beta$-lactam), 1740 (C=O imidazolidinyl), 1720 (CO$_2$H), 1440 (N-N=O) and 1090 cm$^{-1}$ (N—N=O).

$^1$H-NMR (CDCl$_3$) $\delta=7.3$ (m, 5H, C$_6$H$_5$), 5.56 (d, 1H, J=4 Hz, H-5), 5.45 (sa, 1H, CH—C$_6$H$_5$), 4.95 (da, J=4 Hz, H-6), 4.55 (s, 1H, H-3), 3.8 (s, 3H, CO$_2$CH$_3$), 2.10 (s, 6H, CH$_3$ imidazoline), 1.65 (s, 3H, CH$_3$ $\beta$) and 1.5 ppm (s, 3H, CH$_3$-$\alpha$) UV (Cl$_3$CH) $\lambda$ max.=242 nm.

EXAMPLE 4

METHYL (4R,5R,6R,4'R)-6-(2',2'-DIMETHYL-3'-NITROSO-5'-OXO-4'-PHENYL-IMIDAZOLIDIN-1'-YL)-3,3-DIMETHYL-7-OXO-4-THIA-1-AZABICYCLO[3,2,0]HEPTANE-2-CARBOXYLATE 4-OXIDE (XI)

A current of ozone is passed for 30 minutes over a solution of 4.3 g (10 mmol) of methyl (5R,6R,4'R)-6-(2',2'-dimethyl-3'-nitroso-5'-oxo-4'-phenyl-imidazolidin-1'-yl)-3,3-dimethyl-7-oxo-4-thia-1-azabicyclo[3,2,0]heptane-2-carboxylate in 100 ml of methylene chloride, while cooling takes place in a bath of solid carbon dioxide. The product of the heading is obtained by subsequent evaporation. M.p. 129°–131° C.

IR (Nujol) $\nu=1800$ (C=O $\beta$-lactam), 1740 (C=O imidazolidinyl), 1720 (CO$_2$R), 1440 (N—N=O) and 1060 cm$^{-1}$ (SO).

$^1$H-NMR (CDCl$_3$) $\delta=7.3$ (m, 5H, C$_6$H$_5$), 5.5 (s, 1H, CH—C$_6$H$_5$), 5.1 (d, J=4 Hz, 1H, H-6), 4.75 (d, J=4 Hz, 1H, H-5), 4.5 (s, 1H, H-2), 3.8 (s, 3H, CO$_2$CH$_3$), 2.2 (s, 6H, 2CH$_3$ imidazolidine), 1.6 (s, 3H, CH$_3$ $\beta$) and 1.2 ppm (s, 3H, CH$_3$ $\alpha$) UV (CHCl$_3$) $\lambda$ max.=242 nm.

EXAMPLE 5

METHYL (5R,6R,4'R)-6-(2',2'-DIMETHYL-3'-NITROSO-5'-OXO-4'-PHENYL-IMIDAZOLIDIN-1'-YL)-3,3-DIMETHYL-7-OXO-4-THIA-1-AZABICYCLO[3,2,0]HEPTANE-2-CARBOXYLATE 4-OXIDE (XI)

A solution of 0.43 g (1 mmol) of methyl (5R,6R,4'R)-6-(2',2'-dimethyl-3'-nitroso-5'-oxo-4'-phenyl-imidazolidin-1'-yl)-3,3-dimethyl-7-oxo-4-thia-1-azabicyclo[3,2,0]heptane-2-carboxylate in 5 ml of methylene chloride is cooled in a bath of solid carbon dioxide and 0.6 ml of peracetic acid is added slowly up to 40%. Stirring takes place for 3 hours at room temperature, at the end of which it is washed successively with water and saturated sodium chloride solution. After drying over anhydrous magnesium sulphate and evaporation of the solvent, the product of the heading is obtained in solid form.

EXAMPLE 6

P-NITROBENZYL (5R,6R)-6-(2',2'-DIMETHYL-3'-NITROSO-5'-OXO-4'-PHENYL-IMIDAZOLIDIN-1'-YL)-3,3-DIMETHYL-7-OXO-4-THIA-1-AZABICYCLO[3,2,0]HEPTANE-2-CARBOXYLATE (X)

A mixture of 4.2 g (10 mmol) of (5R,6R,4'R)-6-(2',2'-dimethyl-3'-nitroso-5'-oxo-4'-phenyl-imidazolidin-1'-yl)-3,3-dimethyl-7-oxo-4-thia-1-azabicyclo[3,2,0]heptane-2-carboxylic acid, 0.9 g (11 mmol) of sodium bicarbonate, 3.4 g (11 mmol) of benzyltributylammonium chloride, 2.16 g (10 mmol) of p-nitrobenzyl bromide and 42 ml of acetonitrile are stirred at room temperature for 1 hour. Then 50 ml of water are added and extraction is carried out with ethyl acetate. The extracts are washed successively with water and a saturated sodium chloride solution. Drying over anhydrous magnesium sulphate and subsequent evaporation are carried out, thereby obtaining the title product in the form of a solid.

EXAMPLE 7

(4R,5R,6R,4'R)-6-(2',2'-DIMETHYL-3'-NITROSO-3'-OXO-4'-PHENYL-IMIDAZOLIDIN-1'-YL)-3,3-DIMETHYL-7-OXO-4-THIA-1-AZABICYCLO[3,2,0]HEPTANE-2-CARBOXYLIC ACID 4-OXIDE (XIa)

A solution of 0.5 g (1.2 mmol) of (5R,6R,4'R)-6-(2',2'-dimethyl-3'-nitroso-5'-oxo-4'-phenyl-imidazolidin-1'-yl)-3,3-dimethyl-7-oxo-4-thia-1-azabicyclo[3,2,0]heptane-2-carboxylic acid in a mixture of 5 ml of acetone and 25 ml of water, adjusted to a pH of 2.7, is cooled in a bath of ice and a current of ozone is passed through for 2 hours. The solvent is evaporated and the aqueous solution is acidified with dilute sulphuric acid to a pH of 2. The precipitate formed is filtered, washed with water and dried in a vacuum, yielding the title product in the form of a white solid. M.p. 160° C. (dec).

IR (Nujol) $\nu = 1800$ (C=O $\beta$-lactam), 1740 (C=O imidazolidinyl), 1720 (CO$_2$H), 1450 (N—N=O), 1080 (N—N=O) and 1050 cm$^{-1}$ (SO).

$^1$H-NMR (DMSO-d$_6$) $\delta = 7.32$ (m, 5H, C$_6$H$_5$), 5.77 (s, 1H, CH—C$_6$H$_5$), 5.72 (d, J=5 Hz, 1H, H-6), 4.83 (d, J=5 Hz, 1H, H-5), 4.30 (s, 1H, H-2), 2.12 (s, 3H, CH$_3$ imidazolidine), 2.05 (s, 3H, CH$_3$ imidazolidine), 1.47 (s, 3H, CH$_3$ $\beta$) and 1.20 ppm (s, 3H, CH$_3$ $\alpha$) UV (MeOH) $\lambda$ max.=205 and 218 nm.

EXAMPLE 8

P-NITROBENZYL (4R,5R,6R,4'R)-6-(2',2'-DIMETHYL-3'-NITROSO-5'-OXO-4'-PHENYL-IMIDAZOLIDIN-1'-YL)-3,3-DIMETHYL-7-OXO-4-THIA-1-AZABICYCLO[3,2,0]HEPTANE-2-CARBOXYLATE 4-OXIDE

A solution of 5 g (11 mmol) of (4R,5R,6R,4'R)-6-(2',2'-dimethyl-3'-nitroso-5'-oxo-4'-phenyl-imidazolidin-1'-yl)-3,3-dimethyl-7-oxo-4-thia-1-azabicyclo[3,2,0]heptane-2-carboxylic acid 4-oxide in 100 ml of N,N-dimethylformamide and 40 ml of dioxane is treated with 3 g (14 mmol) of p-nitrobenzyl bromide and 1.2 g (14 mmol) of sodium bicarbonate, with stirring, for 4 hours at room temperature. Next, it is poured over ice water and the precipitate formed is filtered off, which corresponds to the title product.

EXAMPLE 9

METHYL (4R,5R,6R,4'R)-6-(2',2'-DIMETHYL-3'-NITROSO-5'-OXO-4'-PHENYL-IMIDAZOLIDIN-1'-YL)-3,3-DIMETHYL-7-OXO-4-THIA-1-AZABICYCLO[3,2,0]HEPTANE-2-CARBOXYLATE 4-OXIDE (XI)

5 g (11 mmol) of (4R,5R,6R,4'R)-6-(2',2'-dimethyl-3'-nitroso-5'-oxo-4'-phenyl-imidazolidin-1'-yl)-3,3-dimethyl-7-oxo-4-thia-1-azabicyclo[3,2,0]heptane-2-carboxylic acid 4-oxide are reacted with 1 ml (16 mmol) of methyl iodide, in accordance with the procedure described in Example 5, thereby yielding the title product.

EXAMPLE 10

METHYL (6R,7R,4'R)-6-(2',2'-DIMETHYL-3'-NITROSO-5'-OXO-4'-PHENYL-IMIDAZOLIDIN-1'-YL)-3-EXOMETHYLEN-8-OXO-5-THIA-1-AZABICYCLO[4,2,0]OCTANE-2-CARBOXYLATE 5-OXIDE (XIII)

A mixture of 2.5 g (5.5 mmol) of methyl (4R,5R,6R,4'R)-6-(2',2'-dimethyl-3'-nitroso-5'-oxo-4'-phenyl-imidazolidin-1'-yl)-3,3-dimethyl-7-oxo-1-aza-4-thiabicyclo[3,2,0]heptane-2-carboxylate 4-oxide, 1.5 g (11 mmol) of N-chlorosuccinimide and 1.8 ml (26 mmol) of propylene oxide in 180 ml of dry carbon tetrachloride is heated between 60° and 80° C. for 2 hours under nitrogen. The solvent is evaporated and the residue obtained is dissolved in 50 ml of dry benzene and is cooled in an ice bath. The precipitate formed is filtered off and a solution of 1.5 ml (12 mmol) of tin tetrachloride in 5 ml of dry benzene is added onto the filtrate which is then stirred for 14 hours at room temperature. The precipitate formed is filtered off and washed with benzene. Once it is dry it is stirred with 25 ml of methanol in an ice bath for 5 hours. The solvent is evaporated and 50 ml of ethyl acetate and 50 ml of water are added. The organic phase is decanted, and is dried over anhydrous magnesium sulphate and is subsequently evaporated, yielding the product of the heading as a mixture of diastereoisomers, which are separated by high-pressure liquid chromatography, using an ethyl acetate-hexane mixture in a 2:1 proportion as an eluent.

The isomer 5S is obtained in the form of a foam. IR (Nujol) $\nu=1790$ (C=O $\beta$-lactam), 1740 (C=O imidazolidinyl) and 1720 cm$^{-1}$ (CO$_2$R).

$^1$H-NMR (CDCl$_3$) $\delta = 7.3$ (m, 5H, C$_6$H$_5$), 5.7 (sa, 1H, =CH$_2$), 5.55 (sa, 1H, CH—C$_6$H$_5$), 5.45 (sa, 1H, =CH$_2$), 5.2 (s, 1H, H-4), 5.05 (m, 2H, H-6 and H-7), 3.8 (s, 3H, CO$_2$CH$_3$), 3.7 (q, 2H, H-2) and 2.25 ppm (s, 6H, 2CH$_3$ imidazolidine) UV (CHCl$_3$) $\lambda$ max.=232 and 240 nm.

The isomer 5R is separated as a colourless foam.

IR (Nujol) $\nu=1790$ (C=O $\beta$-lactam), 1740 (C=O imidazolidinyl) and 1720 cm$^{-1}$ (CO$_2$R).

$^1$H-NMR (CDCl$_3$) $\delta = 7.3$ (m, 5H, C$_6$H$_5$), 5.5 (s, 1H, CH—C$_6$H$_5$), 5.45 (s, 1H, =CH$_2$), 5.4 (s, 1H, =CH$_2$), 5.1 (s, 1H, H-4), 5.05 (d, J=4.5 Hz, 1H, H-7), 4.8 (d, J=4.5 Hz, 1H, H-6), 3.65 (q, 2H, H-2), 2.15 (s, 3H, CH$_3$ imidazolidine) and 2.05 ppm (s, 3H, CH$_3$ imidazolidine) UV (CHCl$_3$) $\lambda$ max.=232 and 240 nm.

EXAMPLE 11

P-NITROBENZYL (6R,7R,4'R)-7-(2',2'-DIMETHYL-3'-NITROSO-5'-OXO-4'-PHENYL-IMIDAZOLIDIN-1'-YL)-3-EXOMETHYLEN-8-OXO-5-THIA-1-AZABICYCLO[4,2,0]HEPTANE-2-CARBOXYLATE 5-OXIDE (XIII)

A suspension of 4 g (7 mmol) of p-nitrobenzyl (4R,5R,6R,4'R)-6-(2',2'-dimethyl-3'-nitroso-5'-oxo-4'-phenyl-imidazolidin-1'-yl)-3,3-dimethyl-7-oxo-4-thia-1-azabicyclo[3,2,0]heptane-2-carboxylate 4-oxide in 150 ml of 1,2-dichloroethane is treated with 2.7 g (20 mmol) of N-chlorosuccinimide and 3 ml of propylene oxide between 60° and 80° C. for 4 hours under nitrogen. The mixture is concentrated to 1/5 of the total volume and cooled in an ice bath. The succinimide is filtered off and the solvent is evaporated. The residue obtained is dissolved in a mixture of 100 ml of toluene and 10 ml of ether and, cooling in an ice bath, a solution of 1.6 ml (14 mmol) of tin tetrachloride in 10 ml of toluene is added. The mixture is stirred for 20 hours at room temperature, at the end of which the precipitate formed is filtered off and washed with toluene. Once it is dry it is stirred in an ice bath together with 100 ml of isopropanol for 1 hour, precipitating the title product, as a mixture of the R and S sulphoxides, which can be separated by high-pressure liquid chromatography, using ethyl acetate-hexane mixture in a 2:1 proportion as an eluent.

EXAMPLE 12

METHYL (6R,7R,4'R)-7-(2',2'-DIMETHYL-3'-NITROSO-5'-OXO-4'-PHENYL-IMIDAZOLIDIN-1'-YL)-3-EXOMETHYLEN-8-OXO-5-THIA-1-AZABICYCLO[4,2,0]OCTANE-2-CARBOXYLATE 5-OXIDE (XIII)

35 ml (50 mmol) of propylene oxide and 400 ml of dry toluene are added to a mixture of 5 g (11 mmol) of methyl (4R,5R,6R,4'R)-6-(2',2'-dimethyl-3'-nitroso-5'-oxo-4'-phenyl-imidazolidin-1'-yl)-3,3-dimethyl-7-oxo-4-thia-1-azabicyclo[3,2,0]heptane-2-carboxylate 4-oxide and 4 g (22 mmol) of N-chlorophthalimide. The mixture is heated to 70°-80° C. for 3 hours under nitrogen, and then left to reach room temperature, thereby causing phthalimide to precipitate, which is filtered off. The filtrate is added into a solution of 2.8 ml (23 mmol) of tin tetrachloride in 10 ml of dry toluene, while it is cooled in an ice bath. It is stirred for 15 hours at room temperature. After this final process, the product of the heading is obtained, as a mixture of the R and S sulphoxides which can be separated by high-pressure liquid chromatography, using an ethyl acetate-hexane mixture in a 3:1 proportion as an eluent.

EXAMPLE 13

METHYL (5R,6R,7R,4'R)-7-(2',2'-DIMETHYL-3'-NITROSO-5'-OXO-4'-PHENYL-IMIDAZOLIDIN-1'-YL)-3-HYDROXY-8-OXO-5-THIA-1-AZABICYCLO[4,2,0]OCT-2-ENE-2-CARBOXYLATE-5-OXIDE (XIV)

A mixture of 0.4 g (0.9 mmol) of methyl (5R,6R,7R,4'R)-7-(2',2'-dimethyl-3'-nitroso-5'-oxo-4'-phenyl-imidazolidin-1'-yl)-3-exomethylen-8-oxo-5-thia-1-azabicyclo[4,2,0]octane-2-carboxylate 5-oxide in 80 ml of methylene chloride is cooled in a bath of solid carbon dioxide and an ozone current is passed through it until a blue colour appears. Next, sulphur dioxide is passed through for 2 minutes and the solvent is evaporated, yielding the title product in the form of a white foam.

IR (Nujol) $\nu=3300$ (OH), 1800 (C=O $\beta$-lactam), 1720 (C=O imidazolidine), 1710 (CO$_2$R) and 1060 cm$^{-1}$ (SO).

$^1$H-NMR (CDCl$_3$) $\delta = 7.3$ (m, 5H, C$_6$H$_5$), 5.55 (s, 1H, CH—C$_6$H$_5$), 5.1 (d, J=4.5 Hz, 1H, H-7), 4.8 (d, J=4.5 Hz, 1H, H-6), 3.95 (s, 3H, CO$_2$CH$_3$), 3.8 (br.s., 1H, OH, interchanges D$_2$O), 3.7 (q, 2H, H-2), 2.28 (s, 3H, CH$_3$ imidazolidine) and 2.25 ppm (s, 3H, CH$_3$ imidazolidine).

EXAMPLE 14

METHYL (5R,6R,7R,4'R)-7-(2',2'-DIMETHYL-3'-NITROSO-5'-OXO-4'-PHENYL-IMIDAZOLIDIN-1'-YL)-3-HYDROXY-8-OXO-5-THIA-1-AZABICYCLO[4,2,0]OCT-2-ENE-2-CARBOXYLATE 5-OXIDE (XIV)

A solution of 0.5 g (1.1 mmol) of methyl (5R,6R,7R,4'R)-7-(2',2'-dimethyl-3'-nitroso-5'-oxo-4'-phenyl-imidazolidin-1'-yl)-3-exomethylen-8-oxo-5-thia-1-azabicyclo[4,2,0]octane-2-carboxylate 5-oxide in 50 ml of methylene chloride is cooled in a bath of solid carbon dioxide and an ozone current is passed through it for some minutes until a blue colour appears. Next, oxygen is passed through for 1-2 minutes and 0.3 g (2.9 mmol) of sodium bisulphite is added. The mixture is stirred in an ice bath until a reaction with potassium iodide is negative. The solid in suspension is filtered off and the filtrate is then evaporated. The title product is thereby obtained in the form of a white foam.

IR (Nujol) $\nu=3300$ (OH), 1800 (C=O $\beta$-lactam), 1740 (C=O imidazolidinyl), 1710 (CO$_2$R) and 1040 cm$^{-1}$ (SO).

$^1$H-NMR (CDCl$_3$) $\delta = 7.3$ (m, 5H, C$_6$H$_5$), 5.45 (s, 1H, CH—C$_6$H$_5$), 5.05 (d, J=4.5 Hz, 1H, H-7), 4.6 (d, J=4.5 Hz, 1H, H-6), 3.9 (s, 3H, CO$_2$CH$_3$), 4.0 (q, 2H, H-2), 2.8 (sa, 1H, OH, interchanges D$_2$O), 2.15 (s, 3H, CH$_3$ imidazolidine) and 2.1 ppm (s, 3H, CH$_3$ imidazolidine).

EXAMPLE 15

P-NITROBENZYL (5S,6R,7R,4'R)-7-(2',2'-DIMETHYL-3'-NITROSO-5'-OXO-4'-PHENYL-IMIDAZOLIDIN-1'-YL)-3-HYDROXY-8-OXO-5-THIA-1-AZABICYCLO[4,2,0]OCT-2-ENE-2-CARBOXYLATE-5-OXIDE (XIV)

A solution of 0.5 g (8.8 mmol) of p-nitrobenzyl (5S,6R,7R,4'R)-7-(2',2'-dimethyl-3'-nitroso-5'-oxo-4'-phenyl-imidazolin-1'-yl)-3-exomethylen-8-oxo-5-thia-1- azabicyclo[4,2,0]octane-2-carboxylate 5-oxide in a mixture of 60 ml of methylene chloride and 10 ml of methanol is cooled in a bath of solid carbon dioxide, and an ozone current is passed through it until a blue colour appears. Next, dry nitrogen is passed through for some minutes. A white solid, which corresponds to the title product, is obtained by evaporation of the solvent.

EXAMPLE 16

METHYL (6R,7R,4'R)-7-(2',2'-DIMETHYL-5'-OXO-4'-PHENYL-IMIDAZOLIDIN-1'-YL)-3-CHLORO-8-OXO-5-THIA-1-AZABICYCLO[4,2,0]OCT-2-ENE-2-CARBOXYLATE (XVI)

0.18 ml (2.2 mmol) of phosphorus trichloride is slowly added to a solution of 0.45 g (1 mmol) of methyl (5S,6R,7R,4'R)-7-(2',2'-dimethyl-3'-nitroso-5'-oxo-4'-phenyl-imidazolidin-1'-yl)-3-hydroxy-8-oxo-5-thia-1-azabicyclo[4,2,0]oct-2-ene-2-carboxylate 5-oxide in 5 ml of dry N,N-dimethyl formamide in a bath of ice. The reaction mixture is stirred for 1 hour at low temperature and for 1 hour at room temperature. It is then poured over ice, precipitating a solid which is filtered off, washed with water and dilute hydrochloric acid and dried in a vacuum, yielding the title product.

Following the previous procedure, starting from methyl (5R, 6R, 7R, 4'R)-7-(2',2'-dimethyl-3'-nitroso-5'-oxo-4'-phenyl-imidazolidin-1'-yl)-3-hydroxy-8-oxo-5-thia-1-azabicyclo[4,2,0]oct-2-ene-2-carboxylate 5-oxide, the product of the heading is obtained in the same way.

IR (Nujol) $\nu = 1790$ (C=O $\beta$-lactam), 1740 (C=O imidazolidinyl), 1720 (CO$_2$R) and 740 cm$^{-1}$ (C—Cl).

$^1$H-NMR (CDCl$_3$) $\delta = 7.4$ (sa, 1H, interchanges D$_2$O, NH), 5.55 (sa, 1H, interchanges D$_2$O, C$\underline{H}$—C$_6$H$_5$), 5.15 (d, J=4.5 Hz, 1H, H-7), 4.85 (d, J=4.5 Hz, 1H, H-6), 3.9 (s, 3H, CO$_2$CH$_3$), 3.8 (q, 2H, H-2), 2.1 (s, 3H, CH$_3$ imidazolidine) and 2.0 ppm (s, 3H, CH$_3$ imidazolidine).

In summary, the exclusive use and property of the invention described above and summarized as follows are claimed:

1. A process for the preparation of 3-chloro-cefem compounds of formula I:

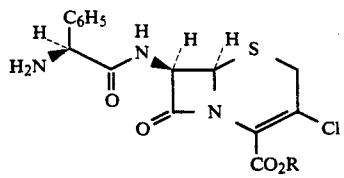

in which R represents hydrogen, or a therapeutically acceptable salt or ester thereof, characterized in that it comprises the following stages:

(1) condensation of the compound of formula VII

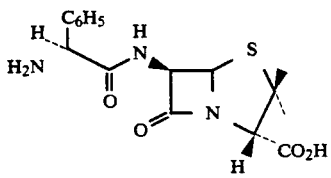

with acetone in the presence of a base followed by nitrosylation in the presence of an acid to produce a compound of formula IX

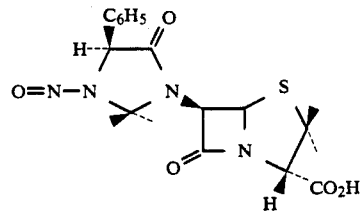

(2) in either order subjecting the product of formula (IX) obtained in the previous stage to esterification in the presence of a polar organic solvent with a halogen derivative of the formula R$^2$-Hal, in which Hal represents halogen and R$^2$ is an ester-forming alkyl or aryl group, and to oxidation, to produce the sulphoxide of formula XI

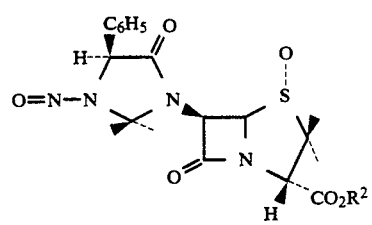

in which R$^2$ has the value indicated above;

(3) treatment of the sulphoxide of formula XI, obtained in the previous stage, first with a halogenating agent to obtain the intermediate sulfinyl chloride of formula XII

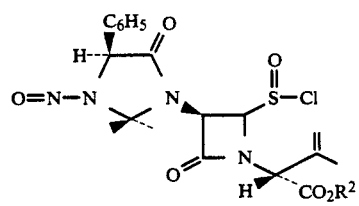

in which R$^2$ is as defined above and Hal is a halogen atom, and subsequently with an acidic compound in order finally to obtain the 3-exomethyl-cefam derivative of formula XIII

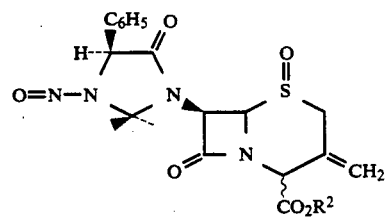

in which R$^2$ is as defined above;

(4) submitting the exomethylene bond of compound XIII, obtained in the previous stage, to oxidative cleavage, to obtain the 3-hydroxycefem derivative of formula XIV

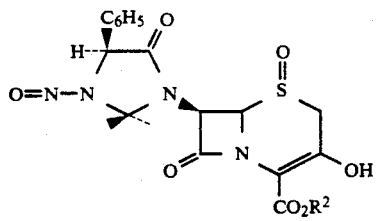

in which $R^2$ is as defined above;

(5) performing the following three reactions: (i) substitution of the hydroxyl group in position 3 by a chlorine atom, (ii) reduction of the sulphoxide group, and (iii) reduction of the N-nitroso group in the lateral chain, by which a compound of formula XVI is obtained

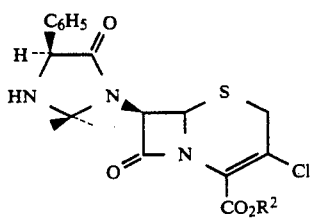

in which $R^2$ is as defined above; and (6) de-protection of the side chain and the carboxyl group, finally separating the product of formula I.

2. The process of claim 1, in which the base used in Stage (1) is a tertiary amine.

3. The process of claim 2, in which the amine is triethylamine.

4. The process of claim 1, in which the agent used in the nitrosylation in Stage (1) is an alkali metal salt of nitrous acid.

5. The process of claim 4, in which the alkali metal salt is sodium nitrite.

6. The process of claim 1, in which the agent used in the esterification in Stage (2) is selected from the group consisting of alkyl halides, benzyl halides and derivatives thereof.

7. The process of claim 6, in which the agent is selected from the group consisting of methyl iodide, benzyl chloride or para-nitrobenzyl bromide.

8. The process of claim 1, in which the esterification which is performed in Stage (2) takes place in the presence of an acid acceptor.

9. The process of claim 8, in which the acid acceptor is selected from the group consisting of potassium bicarbonate or sodium bicarbonate.

10. The process of claim 1, in which the oxidation of the sulphide to sulphoxide in Stage (2) takes place using an ozone-saturated solution as an oxidizing agent in an anhydrous inert solvent at a temperature below 0° C.

11. A process according to claim 1, characterized in that peracetic acid or metachlorobenzoic acid, are used as oxidizing agents in Stage (2).

12. The process of claim 1, in which the intermediate sulphenyl chloride is obtained in Stage (3) by treating the sulphoxide with a halogenating agent selected from the group consisting of N-haloamides and N-haloimides.

13. The process of claim 12, in which the halogenating agent is N-chlorosuccinimide or N-bromosuccinimide.

14. The process of claim 1, in which the solvent used in Stage (3) is selected from the group consisting of halogen derivatives and hydrocarbons.

15. The process of claim 14 in which the solvent is selected from the group consisting of chloroform, 1,2-dichloroethane, benzene and toluene.

16. The process of claim 1, in which the acid used to close the six-member ring in Stage (3) is a compound of the group called Lewis acids.

17. The process of claim 16, in which the Lewis acid is selected from the group consisting of aluminum chloride, tin (IV) chloride and zinc bromide.

18. The process of claim 1, in which the oxidative cleavage in Stage (4) is carried out by treatment with an ozone-saturated solution in an anhydrous inert solvent at a temperature below 0° C.

19. The process of claim 1, in which Stage (5) is carried out by using the reagent formed in the reaction of dimethylformamide with phosphorus trichloride.

20. The process of claim 1, in which the three reactions which constitute Stage (5) are carried out in a single step.

21. The process of claim 1, in which the de-protection of the acetonylidene group of the side chain is carried out by hydrolysis in the presence of an acid.

22. The process of claim 21, in which the acid is trifluoroacetic acid.

23. The process of claim 1, in which the de-protection of the ester group is carried out when R is benzhydryl, trichloroethyl or trialkylsilyl by hydrolysis or by reduction, when R is benzhydryl, p-nitrobenzyl or benzyl.

24. The process of claim 1, in which the product of formula I in which R is H is separated in an aqueous medium with an isoelectric pH.

25. The process for the preparation of 3-chloro-cefem compounds of formula I

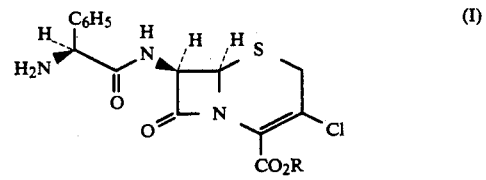

in which R represents hydrogen, or a therapeutically acceptable salt or ester thereof, which comprises the following stages:

(1) condensation of the compound of formula VII

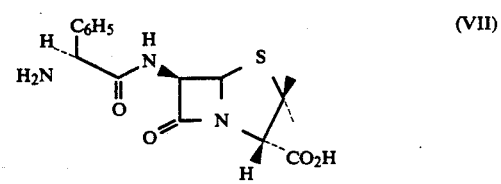

with acetone in the presence of a tertiary amine, followed by nitrosylation with an alkali metal nitrite in an acid medium, to produce a compound of formula IX

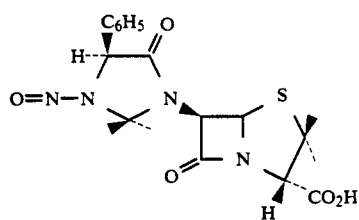

(IX)

(2) in either order subjecting the product of formula (IX) obtained in the previous stage to esterification with a halogen derivative of the formula $R^2$-Hal in which Hal represents halogen and $R^2$ is an ester-forming alkyl or benzyl halide or a derivative thereof in the presence of a basic agent, and to oxidation, by ozone or by a peracid to produce the sulphoxide or formula XI

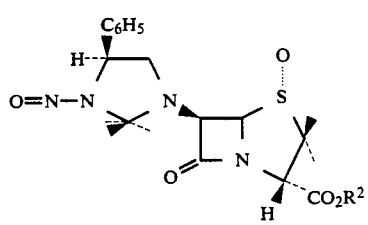

(XI)

in which $R^2$ has the value indicated above;

(3) treatment of the sulphoxide of formula XI, obtained in the previous stage, first with a chlorinating agent comprising an N-chloroamide or N-chloroimide in a solvent selected from the group consisting of chloroform, 1,2-dichloroethane, benzene and toluene to obtain the intermediate sulphenyl chloride of formula XII

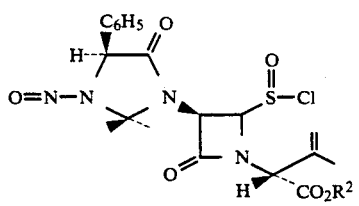

(XII)

in which $R^2$ is as defined above, and subsequently with a Lewis acid in order finally to obtain the 3-exomethylcefam derivative of formula XIII

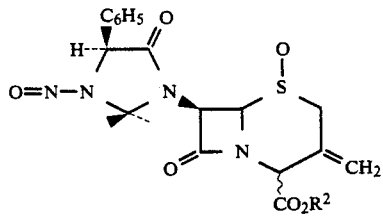

(XIII)

in which $R^2$ is as defined above;

(4) submitting the exomethylene bond of compound XIII, obtained in the previous stage, to oxidative cleavage by ozonolysis, to obtain the 3-hydroxycefem derivative of the formula XIV

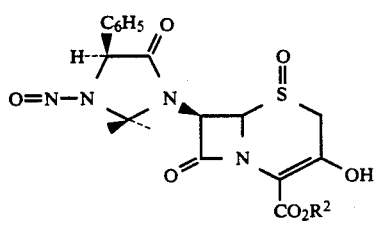

(XIV)

in which $R^2$ is as defined above;

(5) performing the following three reactions in a single step: (i) substitution of the hydroxyl group in position 3 by a chlorine atom using the reagent formed by reaction of dimethyl formamide with phosphorus trichloride, (ii) reduction of the sulphoxide group, and (iii) reduction of the N-nitroso group in the lateral chain, by which a compound of general formula XVI is obtained

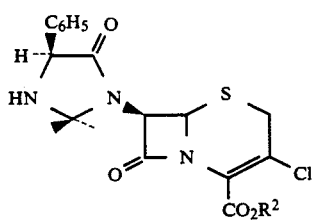

(XVI)

in which $R^2$ is as defined above; and (6) de-protection of the acetonylidene group by hydrolysis in an acid medium and of the carboxyl group by hydrolysis or reduction, finally separating the product of formula I.

* * * * *